United States Patent [19]
Cristobal

[11] Patent Number: 6,132,762
[45] Date of Patent: *Oct. 17, 2000

[54] TRANSCUTANEOUS APPLICATION OF MARIJUANA

[76] Inventor: Walter Cristobal, P.O. Box 372, Bernalillo, N. Mex. 87004

[*] Notice: This patent issued on a continued prosecution application filed under 37 CFR 1.53(d), and is subject to the twenty year patent term provisions of 35 U.S.C. 154(a)(2).

[21] Appl. No.: 09/073,111

[22] Filed: May 5, 1998

Related U.S. Application Data

[60] Provisional application No. 60/045,620, May 5, 1997, abandoned.

[51] Int. Cl.$^7$ ...................................................... A61K 9/70
[52] U.S. Cl. .................. 424/449; 424/401; 424/402; 424/443; 424/447; 514/825; 514/886
[58] Field of Search .............................. 424/195.1, 78.05, 424/401, 402, 447, 449, 443; 514/825, 886

[56] References Cited

U.S. PATENT DOCUMENTS

| | | |
|---|---|---|
| 4,189,491 | 2/1980 | Shapiro et al. . |
| 4,343,798 | 8/1982 | Fawzi . |
| 4,369,190 | 1/1983 | Schulte . |
| 4,476,140 | 10/1984 | Sears et al. . |
| 4,597,961 | 7/1986 | Etscorn . |
| 4,847,290 | 7/1989 | Burnstein . |
| 4,876,276 | 10/1989 | Mechoulam et al. . |
| 4,933,363 | 6/1990 | ElSohly . |
| 5,068,234 | 11/1991 | D'Ambra et al. . |
| 5,338,753 | 8/1994 | Burstein et al. . |
| 5,389,375 | 2/1995 | ElSohly . |
| 5,508,037 | 4/1996 | ElSohly . |
| 5,607,933 | 3/1997 | D'Ambra et al. . |
| 5,635,530 | 6/1997 | Mechoulam et al. . |
| 5,639,460 | 6/1997 | Raymond . |
| 5,716,638 | 2/1998 | Touitou . |

FOREIGN PATENT DOCUMENTS 2 274 588  8/1994  United Kingdom .

OTHER PUBLICATIONS

Touitou et al., Transdermal Delivery of Tetrahydrocannabinol, Int. J. Pharm., 42/1–2 pp. 9–15, 1988.

Formukong et al., Analgesic and Antiinflammatory Activityof Constituents of Cannabis–Saitiva L., Inflammation 12(4) pp. 361–372, 1988.

Zurier, Robert B., "Pre–Clinical Studies Show CT–3 reduces Chronic and Acute Inflammation and Reduces Destruction of Joints", *Arthritis & Rheumatism*, (Jan. 1998).

Jochimsen, PR, RL Lawton, K. VerSteeg and R. Noyes, "Effect of benzppyranoperidine, a DELTA–9THC congener, on pain", *Clinical Pharmacolog & Therapeutics*, vol. 24 (Aug.): pp. 223–227, 1978.

"Developing the Next Generation of Analgesic and Anti–inflammatory Drugs, CT–3", Atlantic Pharmaceuticals, Inc. (www.atlan.com)(1998).

Clark, WC, MN Janal, P. Zeidenberg and G Hahas, "Effects of moderate and high doses of marihuana on thermal pain: sensory decision theory analysis", *Journal of Clinical Pharmacology*, vol. 21 (Aug.–Sep. suppl): pp. 299S–310S (1981).

Weiss, JL, AM Watanabe, L. Lemberger, NR Tamarkin and PV Cardon, "Cardiovascular effects of delta–9 tetrahydrocannabinol in man", *Journal of Clinical Pharmacology*, vol. 13 (Sep.–Oct.): pp. 671–684 (1972).

Goodwin, DW, SY Hill, B. Powell and R. Schwin, "Marihuana: CNS supressant of excitant?", *American Journal of Psychiatry*, vol. 131 (Mar.): pp. 313–315 (1974).

Gill, EW, WDM Paton and RG Pertwee, "Preliminary experiments on the chemistry and pharmacology of cannabis", *Nature*, vol. 228 (Oct. 10): pp. 134–136 (1970).

Dow, GJ, FH Myers, W. Stanton and ML Devine, "Serious reacction s to oral DELTA–9 tetrahydrocannabinol in cancer chemotherapy patients", *Clinical Pharmacology*, vol. 3 (Jan.–Feb.): p. 14 (1984).

Zurier, RB, RG Rossetti, JH Lane, JM Goldber, SA Hunter and SH Burstein, "Dimethylheptyl–THC oic acid: a non-psychoactive antiinflammatory agent with a cannabinoid template structure", *Arthritis & Rheumatism*, vol. 41 (Jan.): pp. 163–170 (1998).

Choy, EH, and DL Scott, "Drug treatment of rheumatic diseases in the 1990s:achievements and future developments", *Drugs*, vol. 53 (Mar.): pp. 337–348 (1997).

Schwartzfarb, L., M. Needle and M. Chavez–Chase, "Dose–related inhibition of leukocyte migration by marihuana and delta 9–tetrahydroncannabinol (THC) in vitro", *Journal of Clinical Pharmacology*, vol. 14 (Jan.): pp. 35–40 (1974).

The Merck Index, An Encyclopedia of Chemical, Drugs and Biologicals, Twelfth Edition, "9349 Tetrahydrocannabinols", Whitehouse Station, New Jersey (1996).

*Primary Examiner*—Thurman K. Page
*Assistant Examiner*—Brian K. Seidleck
*Attorney, Agent, or Firm*—Brian J. Pangrle; Nancy E. Ownbey; Deborah A. Peacock

[57] ABSTRACT

A transcutaneous therapeutic formulation comprising marijuana and a carrier for the treatment of pain, inflammation, arthritis and related disorders in humans and animals.

12 Claims, No Drawings

TRANSCUTANEOUS APPLICATION OF MARIJUANA

CROSS-REFERENCE TO RELATED APPLICATIONS

This application claims the benefit of the filing of U.S. Provisional patent application Ser. No. 60/045,620, entitled Pain Reliever Solution, filed on May 5, 1997 now abandoned, and the specification thereof is incorporated herein by reference.

BACKGROUND OF THE INVENTION

1. Field of the Invention

The present invention relates to the transcutaneous treatment of pain, inflamation and arthritic conditions using marijuana.

2. Background Art

Marijuana contains many compounds, the major psychoactive compound being $\Delta^1$-Tetrahydrocannabinol (THC), also known as $\Delta^9$-THC depending on the carbon numbering convention used (Mechoulam, R., *Science*, 168: 1159–1166, 1970). THC and other compounds in marijuana have been reported to have activities in addition to pyschoactivity. Researchers have reported beneficial activities that cause analgesic, antiemetic, and antiglaucoma effects. However, researchers have not identified all of the compounds and functional groups responsible for these pharmacological effects.

The social stigma and unwanted side-effects associated with recreational marijuana use motivated the search for antipsychoactive THC derivatives and analogs. Since the mid-1970s, scientists have examined various forms of THC, particularly $\Delta^1$-THC metabolites that lack psychoactive properties. For example, researchers have focused recently on dimethylheptyl-THC-11 oic acid (DMH-11C) and its use as a nonpsychoactive antiinflamatory agent (Zurier, R. B., Rosesetti, R. G., Lane, J. H., Goldberg, J. M., Hunter, S. A., Burnstein, S. H., *Arthritis & Rheumatism*, 41:163–170, 1998). When administered orally in a safflower oil carrier, this agent demonstrated antiinflammatory properties in adjuvant-induced polyarthritic rats. The dose level for marked analgesic and antiinflammatory effects was on the order of one microgram of DMH-11C to one kg of body weight. Researchers working on DMH-11C purport a plan for developing parenteral formulations as well (*Developing the Next Generation of Analgesic and Antiinflammatory Drugs*, http://www.atlan.com/anlgesc2.htm, Apr. 23, 1998). However, no one has yet to utilize topical administration of marijuana solutions, THC or agents with a cannabinoid-like structure for the treatment of inflammation or arthritis.

The following patents disclose information in related fields; however, none of these patents disclose the use of transcutaneous or transdermal application of marijuana mixtures or solutions for treating pain, inflammation or arthritic conditions.

U.S. Pat. No. 4,189,491, entitled "Tetrahydrocannabinal in a Method of Treating Glaucoma," issued Feb. 19, 1980, to Shapiro and Cuendet, discloses oral administration of a sub-psychotropic dose of THC to reduce intraocular pressure in glaucoma sufferers.

U.S. Pat. No. 4,476,140, entitled "Composition and Method for Treatment of Glaucoma," issued Oct. 9, 1984, to Sears and Caprioli, discloses a topical treatment to the eye for reducing intraocular pressure using polyoxygenated Labdanes as the active ingredient.

U.S. Pat. No. 4,847,290, entitled "Delta 1-THC-7-OIC Acid and Analgesic and Anti-inflammatory Agents," issued Jul. 11, 1989, to Burnstein, discloses a THC template structure with antiinflammatory and analgesic therapeutic properties. The agent, when administered orally, is nonulcerogenic.

U.S. Pat. No. 4,876,276, entitled "(3S-4S)-7-HYDROXY-$\Delta^6$-TETRAHYDROCANNABINOLS," issued Oct. 24, 1989, to Mechoulam, et al., discloses (3S-4S)-7-hydroxy-$\Delta^6$-tetrahydrocannabinol homologes and derivatives which have analgetic, antiemectic, and antiglaucoma effect when administered orally, by injection, topically for intraocular use or by suppositories.

U.S. Pat. No. 5,389,375, entitled "Stable Suppository Formulations Effecting Bioavailability of $\Delta^9$-THC," issued Feb. 14, 1995, to ElSohly, discloses a suppository formulation containing a $\Delta^9$-THC prodrug ester derivatives in a lipophilic, aprotic lipohilic, paraffin or triacyglyceride carrier base.

U.S. Pat. No. 5,508,037, entitled "Stable Suppository Formulations Effecting Bioavailability of $\Delta^9$-THC," issued Apr. 16, 1996, to ElSohly, discloses a suppository formulation containing a $\Delta^9$-THC prodrug ester for the treatment of pain, spasticity, appetite, depression, anxiety, night vision, and migraine headaches.

U.S. Pat. No. 5,635,530, entitled "(3S-4S)-$\Delta^6$TETRAHYDROCANNABINOL-7-OIC ACIDS and Dervatives Thereof, Processors for Their Preparation and Pharmaceutical Compositions Containing Them," issued Jun. 3, 1997, to Mechoulam, et al, discloses (3S-4S)-$\Delta^6$-tetrahydrocannabinol-7-oic acid derivatives that exhibit analgesic, antiinflamatory, antiemetic, antiglaucoma, leukocyte antiadhesion, and platelet adhesion factor activity.

None of the aforementioned references disclose a topical, transcutaneous treatment derived from the marijuana plant with analgesic, antiinflammatory, antirheumatic, leukocyte antiadhesion or other activities. Only topical ocular, oral, rectal, intravenous and other non-topical treatments are disclosed.

SUMMARY OF THE INVENTION
(DISCLOSURE OF THE INVENTION)

The invention is a formulation comprising a therapeutically effective amount of marijuana and a pharmaceutically acceptable topical, transcutaneous carrier. The carrier comprises at least one member selected from the group consisting of water, alcohol, aldehyde, ketone, carboxylic acid, mineral oil and dimethyl sulfoxide. For an alcohol carrier at least one hydroxyl group per molecule is present. Whether the carrier is an alcohol or other molecule, the carbon chain length, if the carrier contains carbon, is typically between approximately $C_1$ and $C_{24}$. A preferred embodiment of the invention uses isopropanol as the carrier. In general, the carrier comprises at least 1% of the formulation by weight. However, the carrier may comprise guar gum, gelatin, carboxymethylcellulose, carrageenan, agar or the like to modify rate of delivery and other formulation properties.

The dried marijuana weight of the formulation is between approximately 0.01% by weight and 30% by weight and preferably between 0.1% by weight and 10% by weight. A preferred embodiment of the invention uses a carrier comprising isopropanol, between approximately 5% by weight and 99% by weight and preferably between approximately 50% by weight and 80% by weight, and water, between approximately 1% by weight and 100% by weight and preferably between 5% by weight and 100% by weight.

The therapeutic formulation is made by providing and combining a therapeutically effective amount of marijuana with a pharmaceutically acceptable topical, transcutaneous carrier. Initial processing of the marijuana may be accomplished by drying, soaking, crushing, cutting, grinding, and chopping. This is combined with a carrier comprising water, alcohol, aldehyde, ketone, carboxylic acid, mineral oil or dimethyl sulfoxide. The carrier and marijuana can be combined by mixing, blending, steeping, soaking, boiling and the like.

The formulation serves as part of method of treating pain, inflammation, or arthritis comprising transcutaneously applying the formulation to a human or animal body part. The invention aims to treat both human and animal pain, inflammation, arthritis, rheumatoid arthritis, and ailments causing similar bodily distress.

A primary object of the present invention is to relieve pain through the topical, transcutaneous application of a marijuana formulation.

A primary advantage of the present invention is that oral, intravenous, rectal or subcutaneous administration of the therapeutic product is avoided.

A further advantage of the present invention is that the marijuana carrier enhances availability of the active compounds.

Another advantage of the present invention is that the carrier controls transcutaneous absorption of the active marijuana compounds.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS (BEST MODES FOR CARRYING OUT THE INVENTION)

The present invention is directed to a formulation comprising marijuana and a carrier; a method of making or preparing this formulation; and a method of transcutaneously using this formulation to treat pain, inflammation, and arthritis.

The formulation comprises marijuana and a carrier. The marijuana is added to the carrier as described in the method of preparation. The carrier serves two purposes. The first purpose is as a solvent to extract and solubilize the active compounds in marijuana. The second purpose is to control the rate of adsorption through the skin. The latter purpose is discussed in detail below.

For the extraction and solubilization of active marijuana compounds, the carrier comprises water, alcohol, or other hydrophilic and hydrophobic solvents. The weight percentages or volume of carrier and marijuana depend on a variety of factors related to the marijuana and its method of preparation. For a water carrier, the water ranges between approximately 5% by weight and 100% by weight and preferably between approximately 20% by weight and 100% by weight. For an alcohol carrier, the alcohol ranges between approximately 5% by weight and 100% by weight, preferably between approximately 10% by weight and 95% by weight. In addition, the carrier may comprise combinations of more than one type of carrier, e.g., a combination of alcohol and water.

For carriers comprising alcohols, the average carbon chain length of the alcohol preferably falls between approximately C1 and C24. Alcohols with multiple carbon chains may also be used. A preferred embodiment of the invention uses short carbon chain alcohols, preferably from C2 to C12.

For alcohols having only one hydroxyl group, the group utilized may be either a primary, secondary, or tertiary alcohol. For alcohols having more than one hydroxyl group, the groups may appear as primary, secondary, or tertiary alcohols. A preferred embodiment of the invention uses C2 to C12 alcohols having from one to three hydroxyl groups.

In general, appropriate solvents include Dimethylsulfoxide (DMSO), polyethylene glycol, polypropylene glycol, ethanol, propanol, isopropanol, glycerin, and mineral oil. In addition, all solvents may be combined with gel forming compounds such as guar gum, gelatin, carboxymethylcellulose, carrageenan, and agar to produce a lotion or cream for topical administration. Most of these compounds form gels through hydrogen bonding, thus, the use of polar protic solvents is preferable, e.g., isopropanol.

The method of preparing the formulation comprises mixing marijuana with a carrier. The concentration of active constituents in marijuana, as with all plants, varies with respect to genetic characteristics, growing and storage conditions. Thus, the steps performed in preparing the marijuana, and marijuana and carrier formulation, are tailored to the nature and quality of the marijuana used.

A basic first step entails preparation of the plant material. The whole plant may be used for preparing the formulation. Alternatively, the marijuana plant leaves may be separated from the plant stems and seeds; a preprepared extract of the plant's active ingredients; or synthesized marijuana; or active ingredients; or a combination thereof may be used.

For plant material, processing steps such as drying and soaking may be followed by mechanical disruption of the plant material. Typically, dried plant material is ground, cut or crushed to produce small flakes or particles of plant matter whereas soaked plant material is placed in a blender or other processor to disrupt the plant structure. Mechanical disruption processes increase the surface area of the plant material and enhance extraction of the active compounds contained within the marijuana plant. The nature of the marijuana preparation step also affects various subsequent steps. For instance, if the carrier is water, then either drying or soaking in water is an appropriate marijuana preparation step. However, if the carrier possesses hydrophobic qualities, then a drying step is preferably utilized to diminish the plant material's water content before further processing.

Once the plant material is prepared and mixed with the carrier, the entire mixture is preferably heated or agitated, however, heating and agitation are not necessary steps. Heating helps to disrupt the plant cell structure, release the active compounds from with the plant cells, and reduce the processing time. Heating also helps to solubilize the active compounds in marijuana. If the mixture is heated, heating occurs at temperatures from approximately 20° C. to 400° C. and preferably from approximately 20° C. to 110° C. The duration of the heating step is from between approximately minutes to days and preferably from between approximately 5 minutes and 1 day.

Agitation helps to disrupt plant cell structure and increase mass transfer between the plant and the carrier solution. Various forms of agitation are useful ranging from gentle agitation by rolling or shaken to vigorous agitation, e.g., with an impeller blade. A higher energy input to the mixture typically results in better disruption and enhanced mass transfer. The energy input is also a function of agitation time. Typical agitation times vary preferably from between approximately seconds and days and preferably from between approximately 5 seconds and 1 hour.

The marijuana formulation provides for various therapeutic effects including the alleviation of pain, inflammation, and distress associated with arthritis. The method of treatment includes primarily topical administration to the desired body part for transcutaneous absorption of the active compounds. The temperature of the formulation may be adjusted to achieve the desired therapeutic effects. For instance, the formulation may be applied directly with no heating. Alternatively, the formulation may be heated to a temperature between approximately 20° C. and 80° C., and preferably between approximately 25° C. and 65° C., and applied directly to the skin or, the patient may soak the targeted body part in the formulation. Treatment times range from between approximately minutes and hours and preferably between approximately 1 minute and 30 minutes. Alternatively, the formulation may be applied to the patient at room temperature and then the treated area may be heated by a heating pad, water bottle or the like. The temperature and treatment times are approximately the same as those given above.

The invention also provides for application of the formulation combined with cold treatment of the treated area. For instance, a patient may soak in a whirlpool filled with a cold formulation. Soaking times vary from between approximately minutes to hours and preferably between approximately 1 minutes and 1 hour. Use of the formulation at temperatures between approximately −40° C. and 20° C. and preferably between approximately −10° C. and 10° C. may provide therapeutic benefits in addition to cold treatment.

Covering the treated area may also increase efficacy of the formulation. Absorption of many topically applied drugs are enhanced by covering the treated skin with an impermeable plastic sheet or film that hinders evaporation or drug decomposition. The impermeable barrier causes the keratin layer to soften and diminish resistance absorption, thereby facilitating absorption of the drug (*Annual Review of Medicine*, Vol. 33, Ch. 18, 1982, "The Principles of Drug Therapy in Skin Disorders," R. C. Heading, p. 475,476). The formulation delivery mechanism can incorporate a barrier layer made of plastic or film. Alternatively, covering the treated area with cellophane wrap or a similar material can provide similar beneficial increases in formulation efficacy. Treatment methods using a combination of covered and uncovered regimens are within the scope of the present invention.

As discussed above, the formulation may be in the form of a gel. The properties of the gel may be adjusted to control the extraction of active compounds from the marijuana plant material and the rate of transdermal absorption. In general, the transdermal rate of absorption of a drug is increased or decreased depending on the carrier and method of application. Typical carrier solvents for topically administered drugs for transdermal delivery include propylene glycol, glycerin, mineral oil, polyethylene glycol, Dimethylsulfoxide (DMSO) or alcohol. Judicious choice of the carrier is necessary, however, when using a gel formulation. Since many gels are based on hydrogen bonding, the gel may disrupt in the presence of a hydrophilic solvent and negate the intended therapeutic effects.

The gel formulation, as with all formulations covered by this invention, may be placed into a suitable delivery mechanism, e.g., a patch. A delivery mechanism containing the formulation is then placed in the vicinity of the area to be treated. Alternatively, placement of the delivery mechanism in another area, e.g., along an upstream blood or lymph supply route, may provide beneficial treatment as well. Whether applied via a delivery mechanism or directly to the skin, all formulations, including the gel formulation, may be, as described above, heated or cooled to achieve the desired therapeutic effect.

EXAMPLES

Twenty patients with aliments including arthritis, tennis elbow, neck and other joint pain were treated with the formulation of the present invention in a blind study; they were not informed of the composition. Patients were advised to either topically administer the formulation or soak the troubled body area (e.g., arthritic hands) in the given formulation for a period of 10 to 30 minutes. For the first week, patients used the formulation on a daily basis; thereafter, once per week. Patients using the marijuana formulation reported a marked and nearly immediate decrease in pain and inflammation and an increase in joint mobility, some with only one treatment.

The solutions provided to these patients were prepared as follows:

Example I

One ounce of unprocessed marijuana was prepared together with 120 ounces of a solution containing 70% wt. isopropanol and 30% wt. water. The marijuana and isopropanol/water solution was then mixed and let to steep at room temperature, unagitated for at least one hour. After steeping, the plant material was strained from the mixture using cotton cloth. Finally, the mixture was applied to a patient's skin using a clean cotton cloth.

Example II

One half ounce of unprocessed marijuana was prepared together with 12 ounces of a solution containing 70% wt. isopropanol and 30% wt. water. The marijuana and isopropanol/water solution was then mixed and let to steep at room temperature, unagitated for at least one hour. After steeping, the plant material was strained from the mixture using cotton cloth. Finally, the mixture was applied to a patient's skin using a clean cotton cloth.

Example III

One ounce of unprocessed marijuana was prepared together with 120 ounces of water. The marijuana and water solution was then mixed and let to steep at 65° F., unagitated for at least one hour. After steeping, the plant material was strained from the mixture using cotton cloth. Finally, the mixture was applied to a patient's skin using a clean cotton cloth.

Example IV

One half ounce of unprocessed marijuana was prepared together with 12 ounces of water. The marijuana and water solution was then mixed and let to steep at 65° F., unagitated for at least one hour. After steeping, the plant material was strained from the mixture using cotton cloth. Finally, the mixture was applied to a patient's skin using a clean cotton cloth.

The preceding examples can be repeated with similar success by substituting the generically or specifically described reactants, weight percentages, and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of treating joint pain, muscle pain, or arthritis comprising transcutaneously applying a formulation to a human or animal by way of a patch or cloth, the formulation comprising:
   a therapeutically effective amount of an active marijuana compound extracted from the marijuana plant; and
   a transcutaneous carrier selected from the group consisting of water, short carbon chain alcohols, dimethysulfoxide, polyethylene glycol, polypropylene glycol, glycerin, mineral oil and mixtures thereof.

2. The method of claim 1 further comprising the step of applying heat to the human or animal wherein applying heat comprises a member selected from the group consisting of applying heat to a treated area during application of the formulation and applying heat to a treated area after application of the formulation.

3. The method of claim 1 further comprising the step of withdrawing heat from the human or animal wherein withdrawing heat comprises a member selected from the group consisting of withdrawing heat from a treated area during application of the formulation and withdrawing heat from a treated area after application of the formulation.

4. The method of claim 1 further comprising the step of partially covering the human or animal with an impermeable barrier wherein the impermeable barrier comprises a member selected from the group consisting of a patch comprising an impermeable barrier and an impermeable film.

5. The method of claim 4 wherein the impermeable barrier comprises plastic.

6. The method of claim 1 wherein the formulation comprises a gel.

7. The method of claim 6 wherein the gel comprises at least one member selected from the group consisting of guar gum, gelatin, carboxymethylsellulose, carrageenan and agar.

8. The method of claim 1 further comprising the step of heating the formulation.

9. The method of claim 1 further comprising the step of cooling the formulation.

10. A method of treating joint pain, muscle pain, or arthritis comprising transcutaneously applying a formulation to a human or animal by way of soaking a targeted body part of the human or animal in the formulation, the formulation comprising:
    a therapeutically effective amount of an active marijuana compound extracted from the marijuana plant; and
    a transcutaneous carrier selected from the group consisting of water, short carbon chain alcohols, dimethylsulfoxide, polyethylene glycol, polypropylene glycol, glycerin, mineral oil and mixtures thereof.

11. The method of claim 10 further comprising the step of heating the formulation.

12. The method of claim 10 further comprising the step of cooling the formulation.

* * * * *